United States Patent
Okumura et al.

(10) Patent No.: US 7,113,569 B2
(45) Date of Patent: Sep. 26, 2006

(54) X-RAY CT APPARATUS

(75) Inventors: Miwa Okumura, Kuroiso (JP); Yuusuke Toki, Tochigi (JP); Takamasa Ota, Abiko (JP)

(73) Assignees: Kabushiki Kaisha Toshiba, Tokyo (JP); Toshiba Medical Systems Corp., Otawara (JP)

( * ) Notice: Subject to any disclaimer, the term of this patent is extended or adjusted under 35 U.S.C. 154(b) by 0 days.

(21) Appl. No.: 10/724,074

(22) Filed: Dec. 1, 2003

(65) Prior Publication Data

US 2004/0202283 A1    Oct. 14, 2004

(30) Foreign Application Priority Data

Nov. 29, 2002    (JP) ............................. 2002-347795

(51) Int. Cl.
*G21K 1/04*    (2006.01)

(52) U.S. Cl. .................... 378/150; 378/151; 378/19
(58) Field of Classification Search .............. 378/4–20, 378/145–153
See application file for complete search history.

(56) References Cited

U.S. PATENT DOCUMENTS 5,027,380 A * 6/1991 Nishiki ........................ 378/4
5,550,886 A * 8/1996 Dobbs et al. ................. 378/19
6,341,152 B1 * 1/2002 Sugihara ....................... 378/4
6,445,764 B1 * 9/2002 Gohno et al. ................. 378/19
6,778,636 B1 * 8/2004 Andrews ..................... 378/150

FOREIGN PATENT DOCUMENTS

JP    10-248835    9/1998

* cited by examiner

*Primary Examiner*—Edward J. Glick
*Assistant Examiner*—Jurie Yun
(74) *Attorney, Agent, or Firm*—Oblon, Spivak, McClelland, Maier & Neustadt, P.C.

(57) ABSTRACT

An X-ray CT apparatus, as one example, includes at least one X-ray irradiation source configured to irradiate an X-ray to a volume of interest, at least one X-ray detector including a plurality of detection element segments configured to detect the X-ray penetrated through the volume of interest, at least one collimator configured to create an opening that is movable in at least one of a slice direction and a channel direction, at least one image processing part configured to extract a portion of the volume data, a controller configured to set the opening of the at least one collimator to a second opening size according to a cylinder-like second scanning range that is set to limit the volume of interest and configured to perform a second scan, and at least one reconstruction part configured to reconstruct image data based on data collected by the second scan.

9 Claims, 14 Drawing Sheets

SECOND SCANNING RANGE

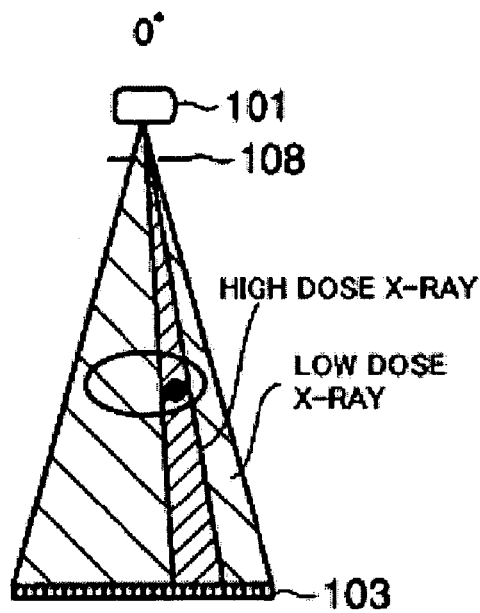
FIG. 11A
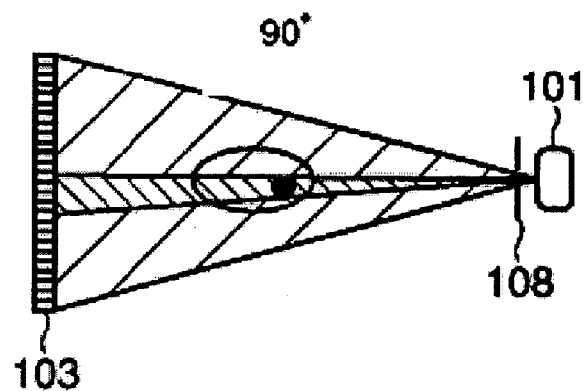
FIG. 11B
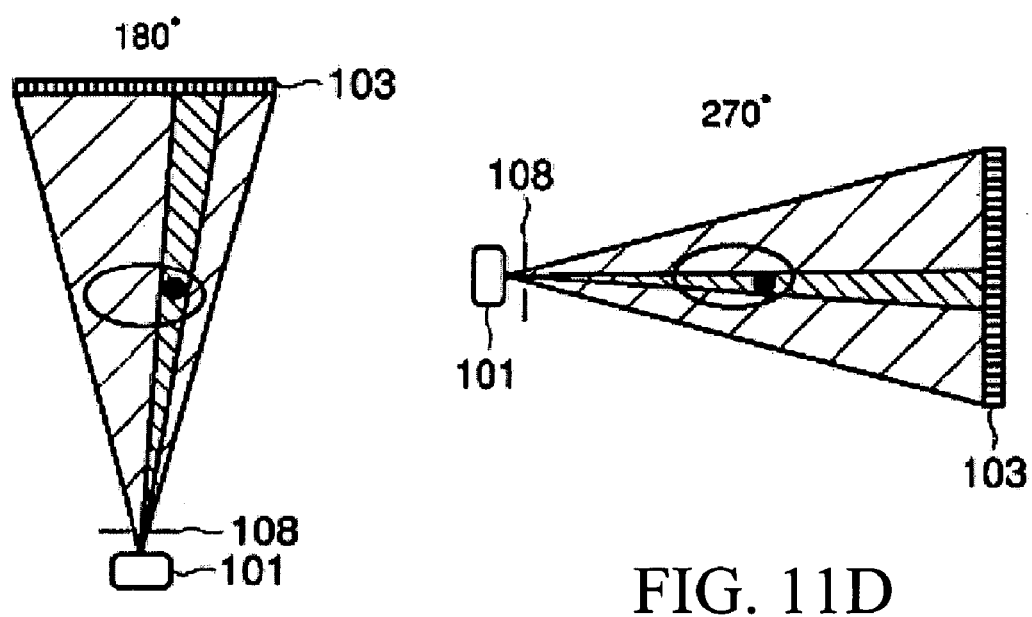
FIG. 11C
FIG. 11D

X-RAY CT APPARATUS

CROSS-REFERENCE TO RELATED APPLICATIONS

This application is based upon and claims the benefit of priority from prior Japanese Patent Application No. 2002-347795 filed on Nov. 29, 2002, the entire contents of which are incorporated herein by reference.

FIELD OF THE INVENTION

The present invention relates to a multi-slice X-ray CT apparatus.

BACKGROUND OF THE INVENTION

X-rays being irradiated to a patient by an X-ray CT apparatus that reconstructs image data from the penetration data is known. With a multi-slice X-ray CT apparatus, it is possible to collect two or more slices of data at once from different positions (multi-slice scanning), using the X-ray detector which has two or more segments of detection elements, such as a combination of a scintillator and a photodiode, which detects the X-rays. By using the multi-slice scan (it is also called a cone beam scan) together with a helical scan, data from a large scanning range can be collected in short time, and the multi-slice X-ray CT apparatus has become popular.

When using the multi-slice scan together with a helical scan, an important issue is the reduction of the X-ray dose. For example, Japanese Patent Publication (Kokai) No. 2002-17716 and Japanese Patent Publication (Kokai) No. 10-248835 describe that a scanning range is set on a scanogram to include an object, such as an internal organ of a patient, an opening of a collimator is set according to the scanning range and a scan is performed of the internal organ. However, in fact, a part of the internal organ may not be included in the scanning range. As a result, insufficient data may be collected and a repeated scan may be necessary.

SUMMARY OF THE INVENTION

The purpose of this invention is to offer a multi-slice X-ray CT apparatus that reduces the X-ray dose received by a patient. In order to ameliorate the above problem, according to one aspect of the present invention, there is provided an X-ray CT apparatus, including: at least one X-ray irradiation source configured to irradiate X-rays to a volume of interest; at least one X-ray detector including a plurality of detection element segments configured to detect the X-rays penetrated through the volume of interest; at least one collimator configured to create an opening that is movable at least in a slice direction and a channel direction; at least one image processing part configured to generate volume data from the detected X-rays and to extract a portion of the volume data corresponding to the volume of interest; at least one controller configured to set the opening of the at least one collimator to a second opening size to irradiate a second scanning range corresponding to the portion of the volume data and configured to perform a second scan of the second scanning range; and at least one reconstruction part configured to reconstruct image data based on data collected by the second scan.

Additionally, an X-ray CT apparatus is provided that includes: at least one X-ray irradiation source configured to irradiate X-rays to a volume of interest; at least one X-ray detector including a plurality of detection element segments configured to detect the X-rays penetrated through the volume of interest; at least one collimator configured to create an opening that is movable at least in a slice direction and a channel direction; at least one image processing part configured to generate volume data from the detected X-rays and to extract a portion of the volume data corresponding to the volume of interest; at least one reconstruction part configured to reconstruct image data based on data collected by a second scan, wherein the at least one collimator comprises, a plurality of movable collimator blades configured to create the opening, and a plurality of auxiliary blades configured to create a slit corresponding to detection element segments other than detection element segments corresponding to the opening.

The present invention also relates to an X-ray CT apparatus, including: at least one X-ray irradiation source configured to irradiate X-rays to a volume of interest; at least one collimator including a first opening configured to transmit the X-rays and a second opening that is more distant than the first opening from a center of the X-rays in both slice and channel directions; at least one X-ray detector including a plurality of detection element segments configured to detect the X-rays that pass through at least one of the first opening and the second opening and that penetrate through the volume of interest; and at least one reconstruction part configured to reconstruct image data based on data collected using the X-rays detected by the at least one X-ray detector.

The present invention also provides a method for reconstructing image data based on data collected by an X-ray CT apparatus that includes at least one X-ray irradiation source configured to irradiate X-rays to a volume of interest, at least one collimator including a first opening through which the X-rays pass and a second opening that is more distant than the first opening from a center of the X-rays in both slice and channel directions, and at least one X-ray detector including a plurality of detection element segments configured to detect the X-rays that pass through at least one of the first opening and the second opening and that penetrate through the volume of interest, the method including: reconstructing image data around the volume of interest based on the X-rays that pass through the first opening; and reconstructing peripheral image data around the image data based on the X-rays that pass through the second opening.

BRIEF DESCRIPTION OF THE DRAWINGS

A more complete appreciation of the invention and many of the attendant advantages thereof will be readily obtained as the same becomes better understood by reference to the detailed description when considered in connection with the accompanying drawings. In the drawings:

FIG. 11A through FIG. 11D are illustrations of opening movement of a collimator in a method B of S6 of FIG. 2;

DETAILED DESCRIPTION OF THE INVENTION

With reference to the drawings, the first non-limiting embodiment of an X-ray CT apparatus of the present invention will be explained. There are many types of X-ray CT apparatus, such as a rotation/rotation type where an X-ray tube and an X-ray detector rotate around a patient as one unit. Another type of X-ray CT apparatus is a fix/rotation type where a plurality of detection elements are arranged in a ring shape and an X-ray tube rotates around a patient. The invention may be applied to each type of X-ray CT apparatus. Hereinafter, a rotation/rotation type X-ray CT apparatus is explained as one example.

A mechanism for changing an incidence X-ray into an electric charge is mainly grouped into a direct conversion type and an indirect conversion type. In the direct conversion type, the X-ray is changed into an optical signal by a fluorescent substance, such as a scintillator, and the optical signal is changed into the electric charge. The indirect conversion type uses a photoconduction phenomenon where a pair of an electron and a hole in a semiconductor is generated by the X-ray and the electron and the hole move to corresponding electrodes. As the X-ray detector, each type may be used. Hereinafter, the indirect type X-ray detector is explained as one example.

In addition, in recent years, a so-called multi-tube type X-ray CT apparatus that includes a plurality of pairs of X-ray tubes and X-ray detectors located in a rotation frame is developing as a commercial product, and surrounding technology is also progressing. The present invention may be applied to a single tube type X-ray CT apparatus or the multi-tube type X-ray CT apparatus, as well as other equivalent devices. Hereinafter, the single tube type X-ray CT apparatus is explained as a non-limiting example.

Figure 1:
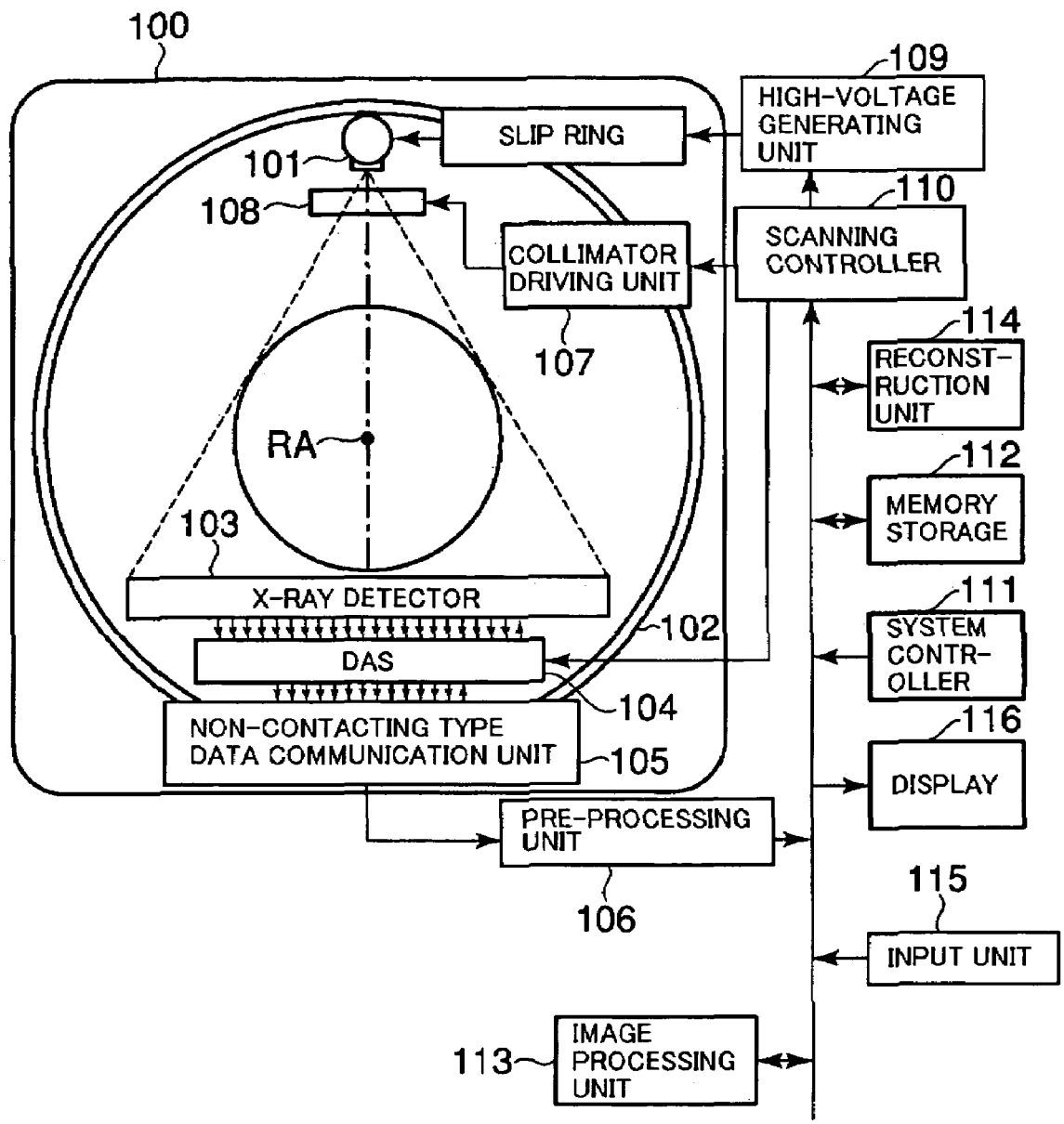
FIG. 1 is a block diagram of an X-ray CT apparatus of one embodiment according to the invention.

FIG. 1 is a block diagram showing the composition of the X-ray CT apparatus of the first embodiment of the present invention. The X-ray CT apparatus has a gantry 100. The gantry 100 has a ring shaped rotation frame 102 that is rotatable around a rotation center axis RA. An X-ray tube 101 is located in the rotation frame 102, and an X-ray detector 103 is located at an opposite side in the rotation frame to the X-ray tube 101 so as to place the rotation center axis is therebetween. The X-ray detector 103 can be used for a multi-slice scanning. That is, the X-ray detector 103 has a plurality of detection element segments that are arranged along a direction parallel to the rotation center axis (slice direction). The number of the detection element segments is 64 segments, for example. It is assumed that a detection width of each detection element in the slice direction is 0.5 mm as a corresponding value on the rotation center axis RA. Each detection element segment has a plurality of detection elements arranged along a channel direction. In addition, it is assumed that a Z-axis is set as the rotation center axis RA, and a XY coordinate system is a rotation coordinate system centering on the Z-axis. In this case, an X-ray center axis that connects a focus of the X-ray tube 101 and a center of the X-ray detector 103 is defined as the Y-axis, and an axis that is perpendicular to the Y-axis and the Z-axis is defined as the X-axis. These X, Y, and Z-axes are used suitably below.

A collimator 108 is located between the X-ray tube 101 and the rotation center axis RA. The collimator 108 is attached to an X-ray radiation window of the X-ray tube 101. The collimator 108 is used as an X-ray limiting device that arbitrarily trims a position and a size of the X-ray generated on the focus of the X-ray tube 101 and irradiated from the X-ray radiation window, and is called an X-ray diaphragm. The collimator 108 has a plurality of members for blocking the X-ray, such as four collimator blades 11 through 14 that are respectively movable along the X or Y-axis, as shown in FIG. 5. The collimator is controlled by a collimator driving unit 107.

A data collection circuit 104 referred to as DAS (Data Acquisition System) is connected to the X-ray detector 103. The data collection circuit 104 changes the output (current signal) of each channel of the X-ray detector 103 into a voltage signal, amplifies the voltage signal, and converts the voltage signal into a digital signal. A pre-processing unit 106 that corrects non-homogeneity between channels of the DAS outputs, etc. is connected to the DAS 104 via a non-contacting type data communication unit 105 using light or magnetism as a medium. The data on which the pre-processing is executed is stored in a memory storage 112. The memory storage 112 is connected to a system controller 111 via a data/control bus as well as to an image reconstruction unit 114 for reconstructing an image based on projection data, a display 116, an input unit 115 including a pointing device, such as a mouse, and a keyboard device, an image-processing unit 113 and a scanning controller 110 for controlling the gantry 100 and a high-voltage generating unit 109.

Figure 2:
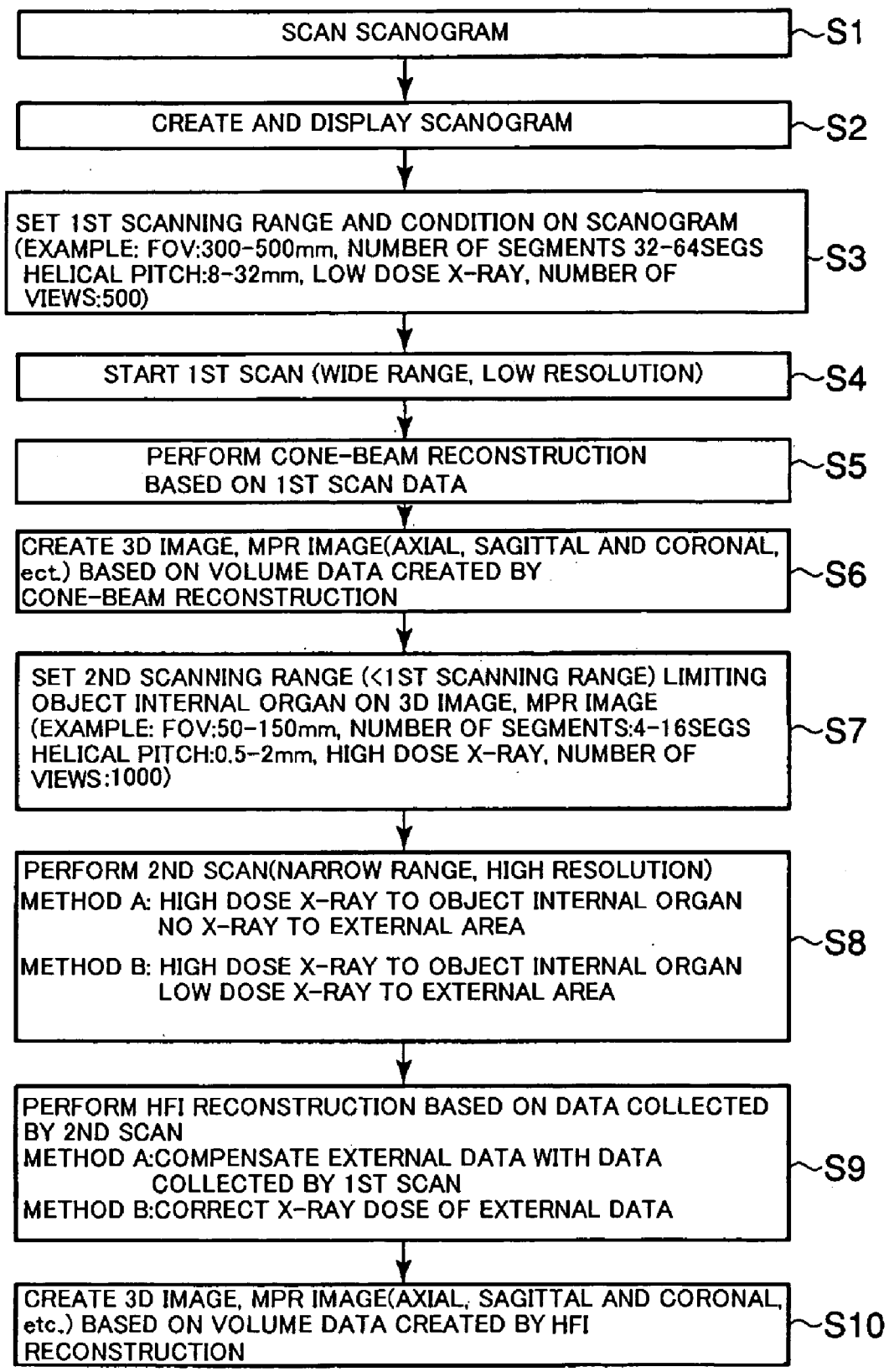
FIG. 2 is a flow chart of a scan and a reconstruction by a scanning expert system of FIG. 1.

FIG. 2 shows a flow of a series of processes of the non-limiting first embodiment. First, a scanogram is taken (Step S1). An imaging of the scanogram is then performed as rotation of the rotation frame 102 stops, the X-ray is generated continuously, a signal is repeatedly read from the X-ray detector 103 at a fixed cycle, and a bed plate moves at a constant speed. Based on the data collected by the scanogram imaging, scanogram data is created in the image-processing unit 113, and the created scanogram data is displayed on the display 116 (Step S2).

Figure 3:
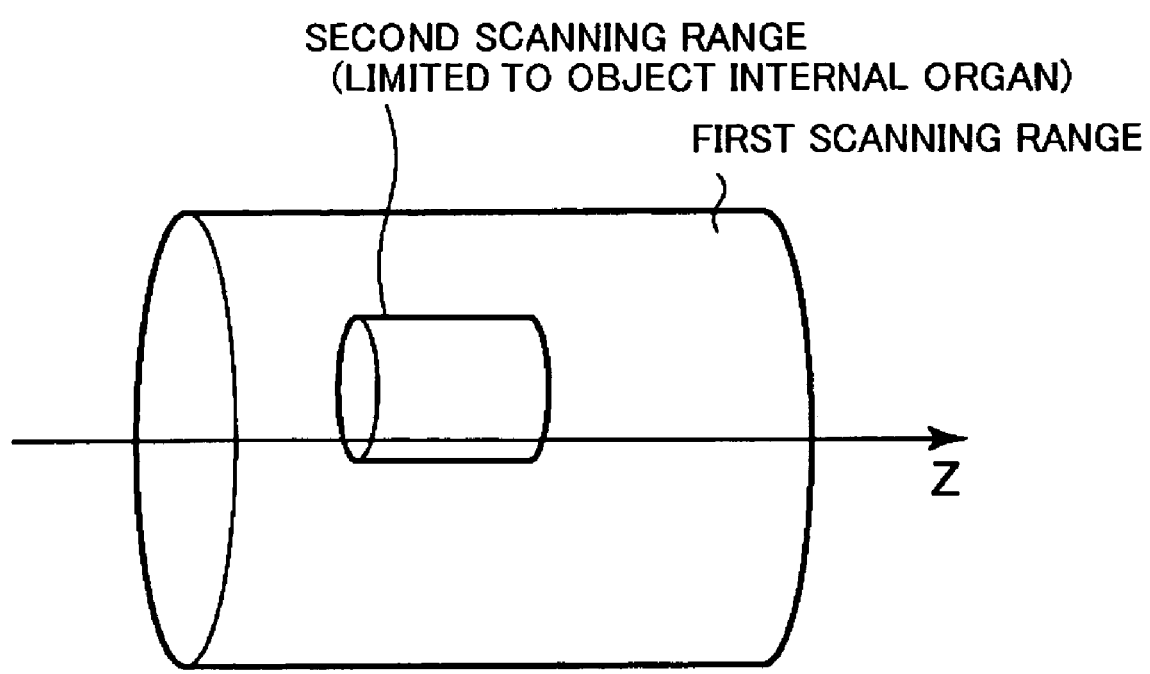
FIG. 3 is an illustration of first scanning range set by S3 of FIG. 2 and second scanning range set by S7 of FIG. 2.

An operator sets a scanning range (first scanning range) shown in FIG. 3 on the displayed scanogram with the input unit 115, and a first scanning condition is also set up (Step S3). In this embodiment, helical scanning is performed at least twice. The first scan is performed for scanning a large area by low resolution, and the second scan aims at scanning a narrow area in which an object internal organ is targeted by high resolution. The first scan is clearly distinguished from the second scan. The first scanning range may, as an example, be a cylinder form, but is set up as a rectangle for showing a main section on the scanogram. For the first scanning range to include a body width of the patient, a radius (FOV) is set in the range of 300 to 500 mm, for example. In addition, the first scanning range is set comparatively long in the body axis direction (slice direction) to include both an object internal organ, such as a heart, and a surrounding internal organ. Moreover, as the first scanning condition, 32 through 64 detection element segments that are comparatively more segments from 64 detection element segments are selected and used. In addition, a helical pitch (a plate movement distance per rotation) is set up comparatively fast, such as in the range of 8 to 32 mm. Additionally, in the first scanning, a tube current value is set as regulation value corresponding to low X-ray dose comparatively by the system controller 111, and in order to compensate for sensitivity decrease by the low X-ray dose, the number of views per rotation is set as 500. The setting range or the regulation value is set by the system controller 111.

Figure 5A:
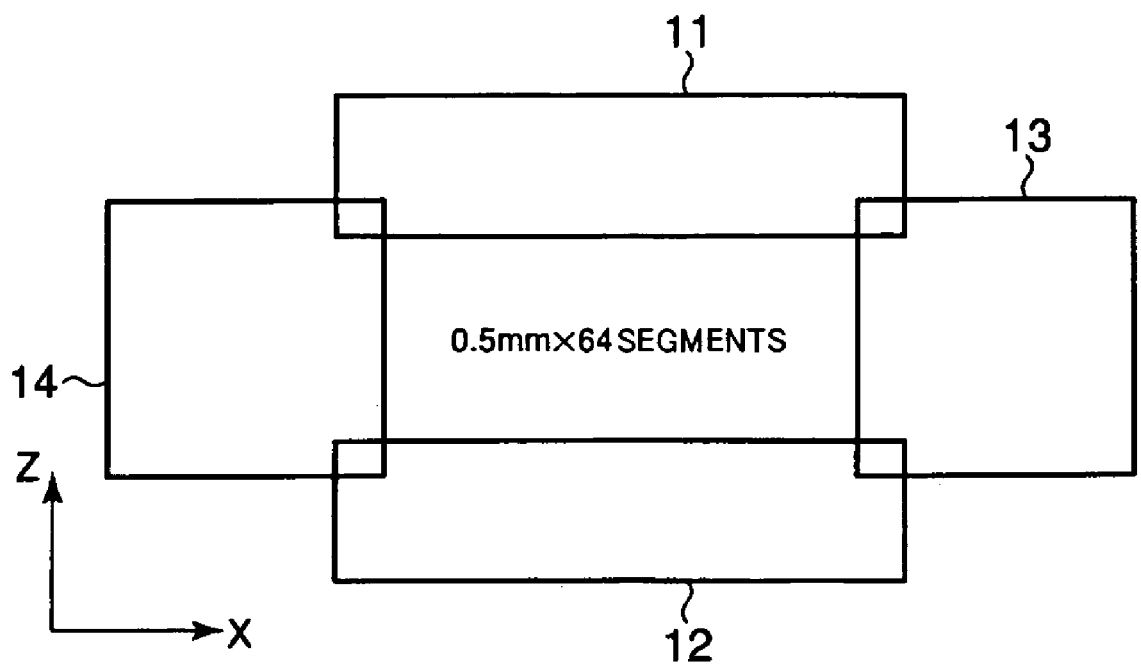
FIG. 5A is an illustration of an opening of during first scanning on S3 of FIG. 2.

The first scanning is performed by the scanning controller 110 under the first scanning condition to the first scanning range (Step S4). In the first scan, as shown in FIG. 5A, the opening of the collimator 108 is set in the X-direction by the width according to the comparatively large diameter of the first scanning range, and is set in the Z-direction by the comparatively long length according to slice width and the number of the segments. That is, a fan angle of the X-ray is set according to the diameter of the first scanning range and a cone angle of the X-ray is set according to the length of the first scanning range.

Based on the projection data of the first scanning range collected by the first scanning, the reconstruction unit 114 performs reconstruction processing (Step S5). Volume data covering a comparatively large area according to the first scanning condition is generated by comparatively low resolution. For example, a cone-beam reconstruction method may be adopted as the reconstruction processing method.

The cone-beam reconstruction method uses an approximate 3-dimensional reconstruction algorithm that is obtained by expanding a mathematically accurate fan-beam reconstruction algorithm (2-dimensional plane) to the Z-axis direction. In the cone-beam reconstruction method, a weighted coefficient corresponding to the Z-coordinate is multiplied by the projection data, and a convolution processing is performed between the weighted data and the same reconstruction function as the fan beam data is applied. Eventually, as a back projection processing, the convolution data is back-projected on a path (from the focus to the channel of the detector) which the X-ray passes, and the back projection processing is repeated for 360°. One such cone-beam reconstruction method is known as the Feldkamp reconstruction method, which extends a reconstruction processing method of a conventional scanning method.

The volume data is used for diagnosis of the object internal organ, the surrounding internal organ and a tissue structure in a large area, and may also be used for setting the scanning range of the second scanning (second scanning range). The image-processing unit 113 extracts an area of the object internal organ, such as the heart (by way of non-limiting example), from the volume data, and a 3-dimentional image (3D image) is created and displayed on the display 116 (Step S6).

Figure 4:
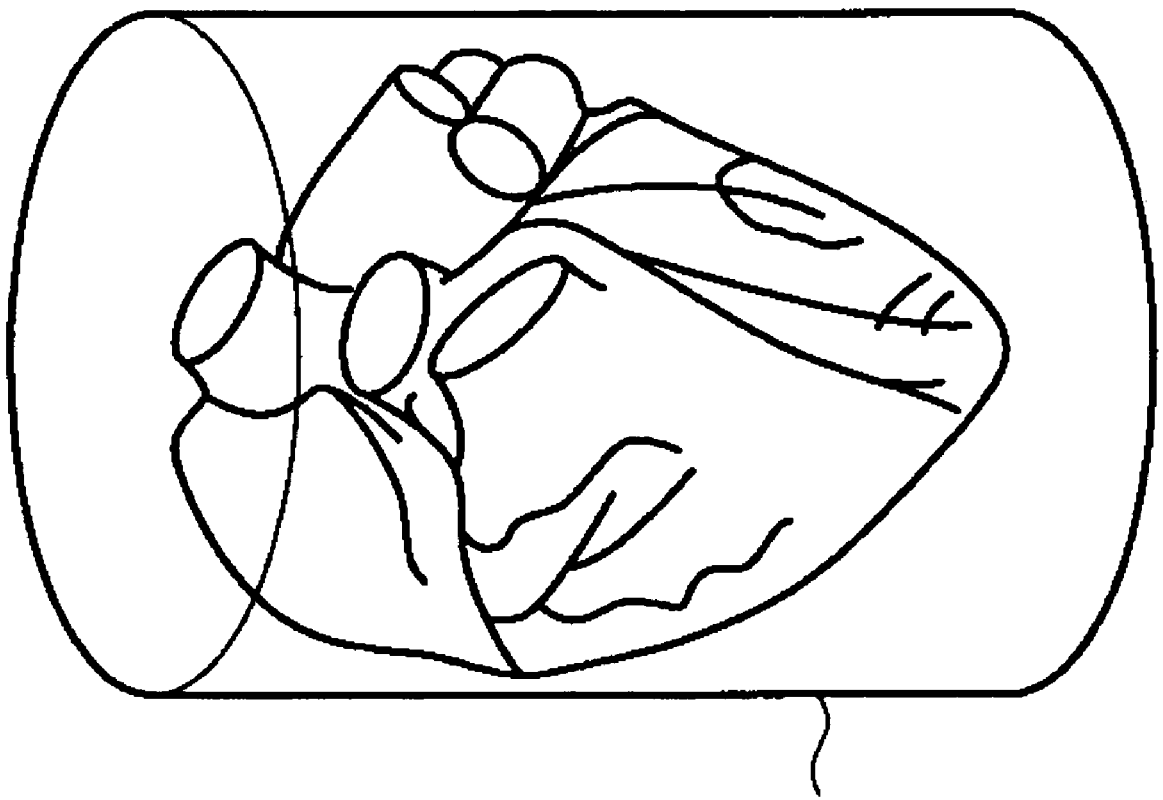
FIG. 4 is an illustration of one example of a display for setting the second scanning range of FIG. 3 on 3D image.

As the 3D image, a surface image or wire frame image is suitable, as shown in FIG. 4. The operator operates the input unit 115 and arbitrarily rotates the 3D image on a screen to set the second scanning range (having an approximate cylinder form) covering the area of the heart in all directions (Step S7). In fact, in consideration of the expansion and contraction movement of the heart, the second scanning range is set larger than the area of the heart, to include a margin.

Although it has been explained that the second scanning range is set on the 3D image, instead of or in addition to the 3D image, an MPR (Multi-Planar Reconstruction) image, such as three tomographic images (axial, coronal, and sagittal images), may be created from the volume data or from the data of the extracted heart area, and the second scanning range may be set on the tomographic images.

Moreover, although it has been explained that the second scanning range is manually set by the operator, the diameter and the length of the second scanning range may be automatically set to include the extracted heart area. In this case, in order to include the above-mentioned margin, expansion processing is performed on the extracted heart area by a predetermined ratio, and the second scanning range is set up to the expanded heart area. The radius (FOV) of the second scanning range is set, for example, in the range of about 50 to 150 mm, so that the heart area (object internal organ) is included, and the second scanning range is set up in the body axis direction (the slice direction) to be comparatively short, so that the heart area is limited with the above-mentioned margin.

Additionally, as the second scanning condition, the number of detection element segments used in the second scan is set comparatively few (i.e., 4–16 segments from 64 segments), and the helical pitch is set, for example, to about 0.5–2.0 mm, corresponding to the comparatively slow plate movement. Moreover, in the second scan, the tube current value is set as the regulation value corresponding to the comparatively high X-ray dose by the system controller 111, and the number of views per rotation may be set as approximately 1000. The setting range or the regulation value is set by the system controller 111. In addition, although it has been explained that the number of detection element segments is selected from the range of about 4–16 segments in the second scan, the number of detection element segments is determined by the limit of the fan-beam reconstruction.

Although the cone-beam reconstruction method includes the correction processing about a cone-angle as mentioned above, the accuracy of the correction cannot be enough, and an artifact may appear. Therefore, although there is little influence on a comparatively low resolution scan like the first scan, the influence cannot be ignored at a comparatively high resolution scan like the second scan.

Therefore, the cone-beam reconstruction method should not be used substantially, and the fan-beam reconstruction method (the fan-beam reconstruction which is used together with the helical filter interpolation method (HFI) is adopted) is adopted. Since the cone-angle is not corrected in the fan-beam reconstruction method, artifacts caused by the cone-angle can occur. The limit for preventing the artifacts caused by the cone-angle from having significant influence is 16 segments (8 mm), for example, and the maximum of the number of used segments is restricted to 16 segments, for example, in the second scan conditions.

Figure 5B:
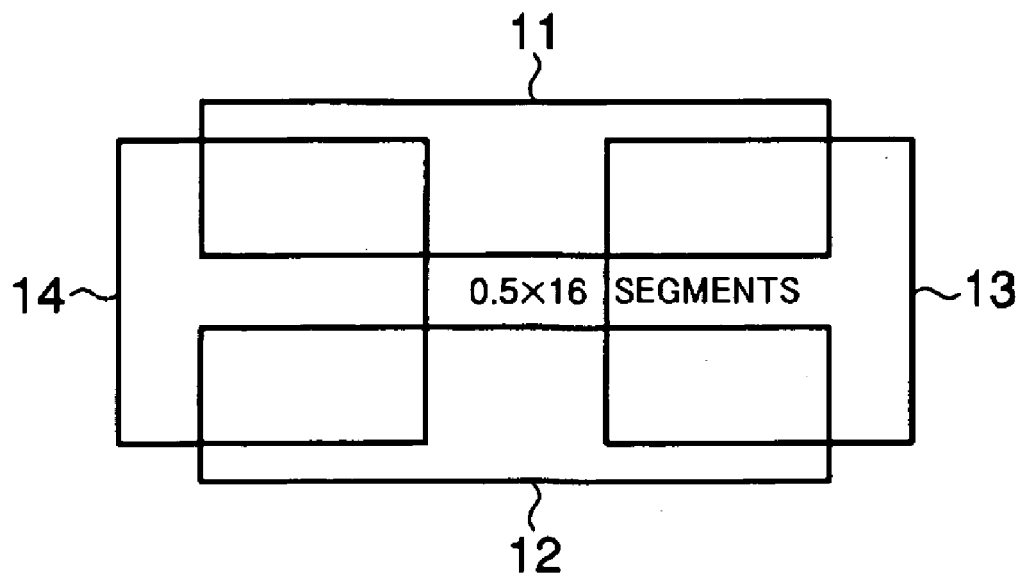
FIG. 5B is an illustration of an opening of during second scanning on S7 of FIG. 2.
Figure 6:
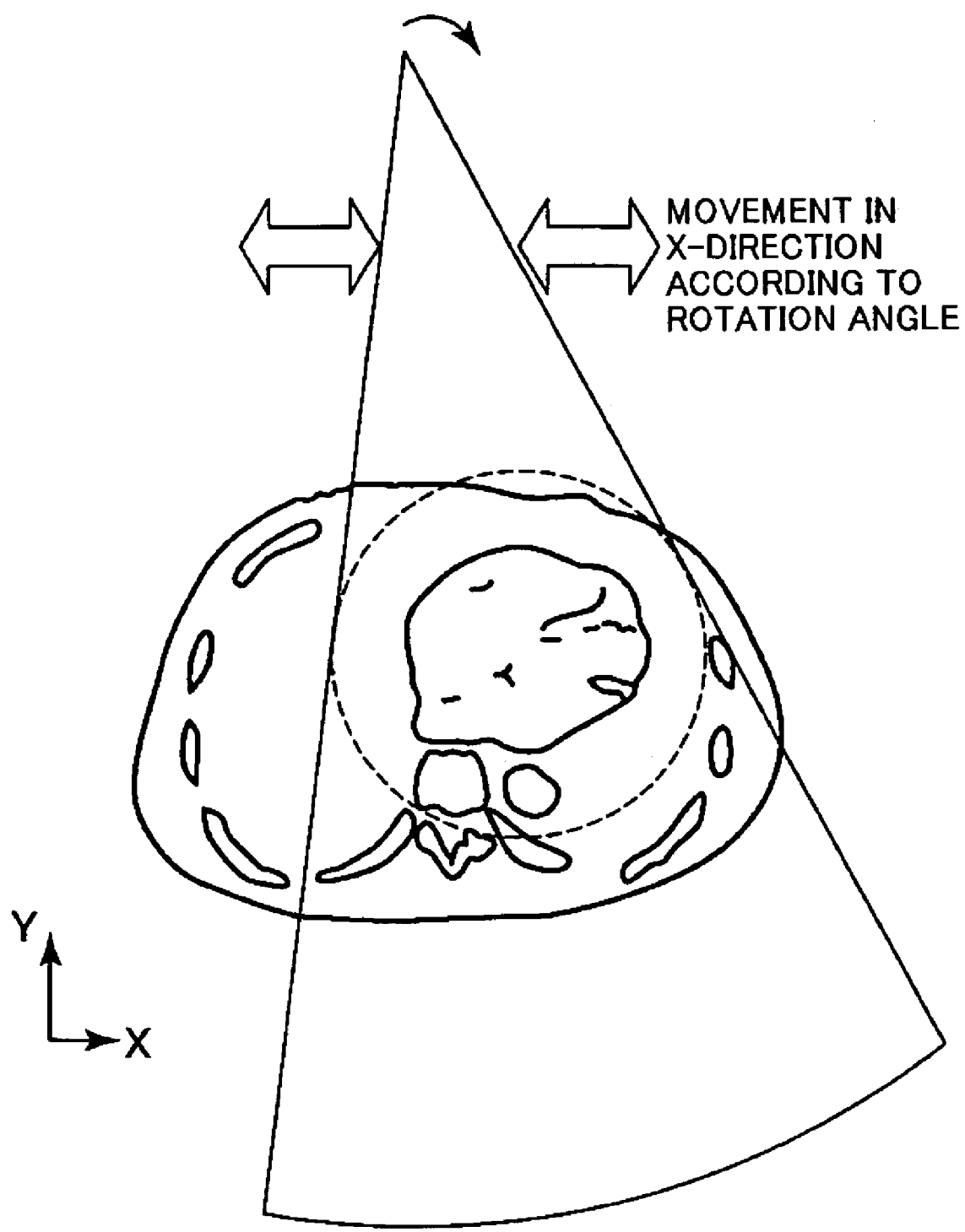
FIG. 6 is an illustration of X-ray limited by a collimator during the second scanning on S7 of FIG. 2.
Figure 7A:
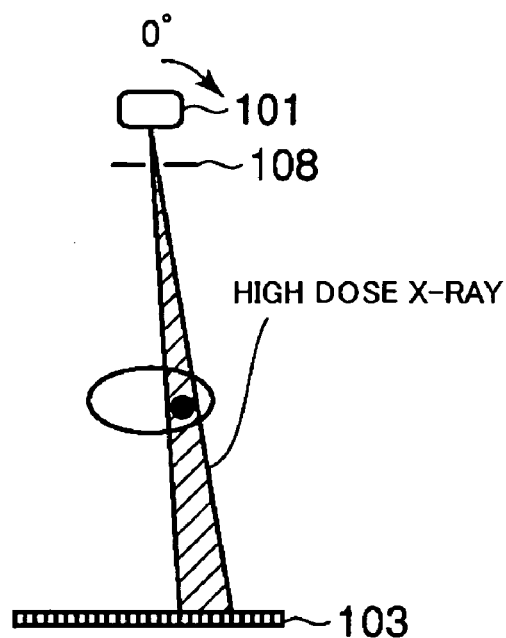
FIG. 7A through FIG. 7D are illustrations of opening movement of a collimator according to rotation of an X-ray tube.
Figure 7B:
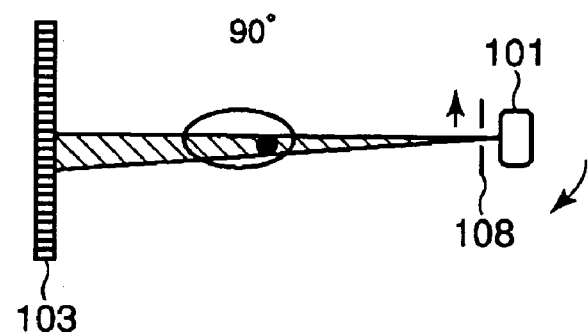
Figure 7C:
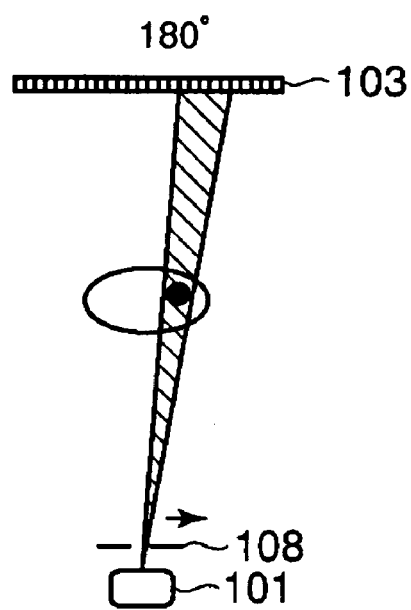
Figure 7D:
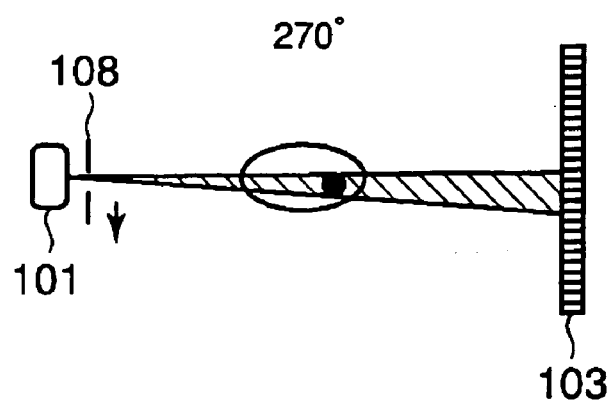

The second scan is performed under the second scanning condition to the second scanning range (Step S8). In the second scan, as shown in FIG. 5B, the opening of the collimator 108 is set in the X-direction by the width according to the comparatively small diameter of the second scanning range under the control of the scanning controller 110, and the opening is set in the Z-direction by the comparatively narrow length according to the slice width and the number of the segments. That is, the fan-angle of the X-ray is set up according to the diameter of the second scanning range, and the cone-angle of the X-ray is set up according to the length of the second scanning range. If necessary, by using a shift function in Y-direction of the X-ray tube 101 and the X-ray detector 102 and by increasing the number of the channels of the second scanning range to more than before or the maximum, the resolution can be improved.

Although the X-ray tube 101 and the X-ray detector 103 rotate around the patient, the center axis of the second scanning range that is set for the object internal organ, such as the heart, may shift from the rotation center axis RA of the rotation frame 102. If the rotation frame 102 rotates when the position of the opening of collimator 108 is fixed, it is difficult to scan the second scanning range.

To ameliorate this problem, as shown in FIG. 6 and FIGS. 7A–7D, according to a shift direction and a shift distance of the center axis of the second scanning range to the rotation center axis RA of the rotation frame 102, when the width of the opening of collimator 108 is fixed, the center position of the opening is moved in the X-direction according to the rotation of the X-ray tube 101. When the height and the right-left position of the bed plate is controlled by the system controller 111 so that the center axis of the second scanning range corresponds to the rotation center axis RA of the rotation frame 102, it may not be necessary to move the center position of the opening of the collimator 108 according to the rotation of the X-ray tube 101.

Based on the projection data of the second scanning range that is collected by Step S8, the reconstruction processing is performed in the reconstruction unit 114 (Step S9). Since data in an external range of the second scanning range is not collected in the second scan, the external image cannot be reconstructed. Therefore, the external data of the second scanning range is compensated by the data collected in the first scan as shown by a distribution of the projection data of the view in FIG. 8. As mentioned above, the fan-beam reconstruction method that is used together with the helical filter interpolation method (HFI).

Figure 8:
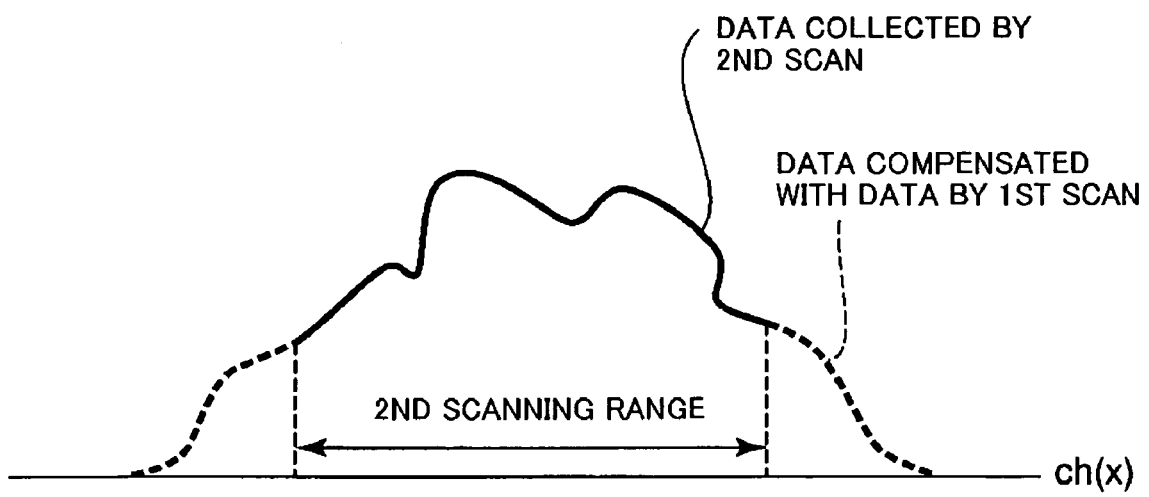
FIG. 8 is an illustration for explaining data correction of a non-irradiation range of an X-ray.

In the helical filter interpolation method, as shown in FIG. 8, a weighted filter function where a weighted coefficient decreases gradually according to the distance from a reconstruction position is convolved to the data collected in a plurality of separated positions near the reconstruction position by each view, and the total is treated as the data on the reconstruction position. When the helical filter interpolation method is used, an effective slice width is given as a total distance of separated positions for the interpolation.

Figure 9:
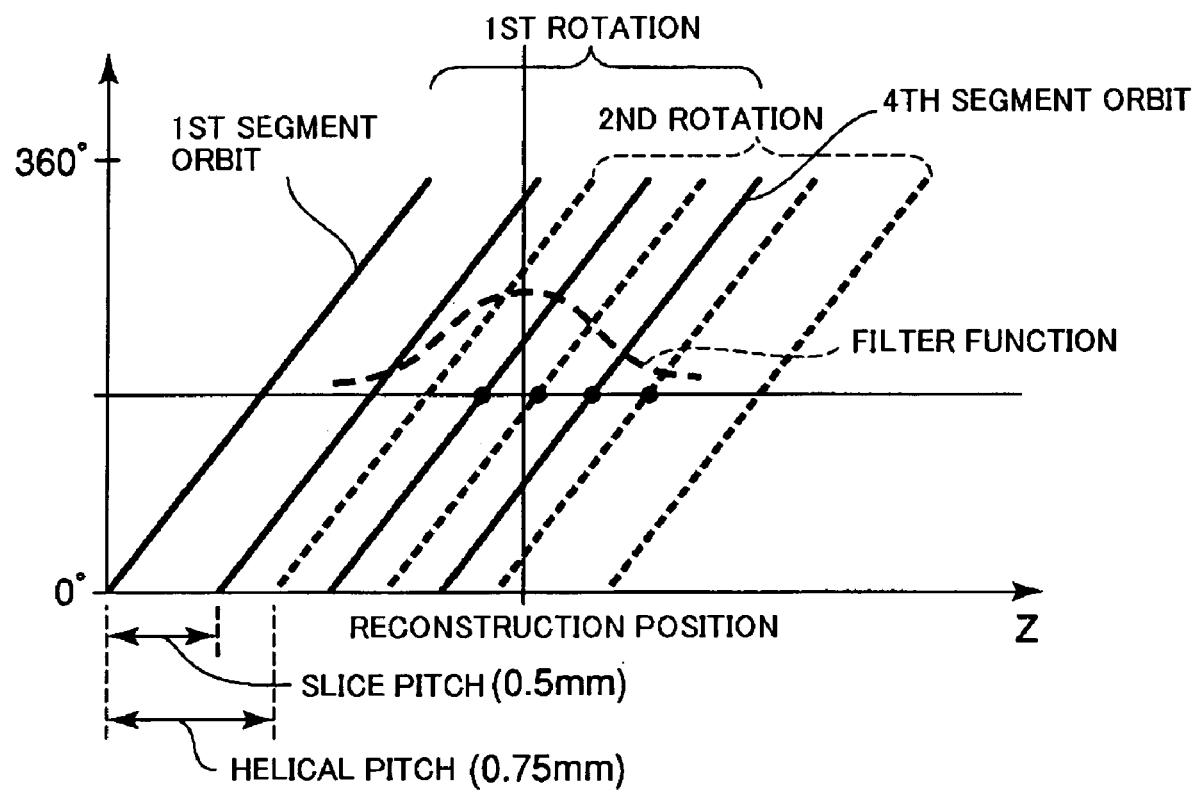
FIG. 9 is an illustration for explaining HFI reconstruction on S8 of FIG. 2.

In order to improve slice resolution by making the effective slice width as thin as possible, as shown in FIG. 9, it is desirable to set the helical pitch at N times (where N is not an even number) the pitch (slice pitch) of the detection element segment, so that an orbit of the detection element segment is located between previous orbits of detection element segments. In FIG. 9, it is shown that N=1.5, for example.

As for the external data of the second scanning range that is collected in the first scan, the data on the reconstruction position is calculated by the helical filter interpolation method based on the data collected by the first scan on a plurality of separated positions near the reconstruction position. In addition, since the X-ray dose is different between the first scan and the second scan, it is desirable to correct the data collected by the first scan or the data calculated by the helical filter interpolation method according to the X-ray dose ratio. Moreover, although data of the view that is collected by the first scan but not by the second scan exists, the data is compensated by the data of the nearest view or the data calculated from data of several near views as the data of the second scan.

Although it has been explained that the external data of the second scanning range, which is not collected in the second scan, is compensated by the data collected in the first scan, the external data of the second scanning range may be compensated by the data collected in the scanogram scan (Step S1). Otherwise, the external data of the second scanning range may be assumed based on the internal data of the second scanning range that is collected in the second scan, such as the data that is averaged between the most outside part data within the second scanning range.

In a heart inspection, an electrocardiographic synchronization method may be used together with the fan-beam reconstruction method. In the electrocardiographic synchronization method, while the scan is repeated over several heart beats, the projection data is stored in relationship to electrocardiographic data collected from the patient. The projection data close in phase to each other are read out among the data from several heart beats, and the image is reconstructed based on the readout projection data of (360°) or (180+the fan-angle degrees). By using the electrocardiographic synchronization method, the influence of the movement caused by the heart beat on the quality of the image can be reduced.

The reconstruction processing is repeated on several reconstruction positions, eventually the volume data is created, and the 3D image, the MPR image, or other arbitrary image is created based on the volume data and displayed in the image-processing unit 113 (Step S10). In the above reconstruction method, the external data of the second scanning range is not collected in the second scan and the external data is compensated by the data collected by the first scan, etc, which is called as "Method A." In the non-limiting embodiment, the following "Method B" may be adopted as an alternative to the method A.

In method B, the external data is collected in the second scan in addition to the internal data. In order to reduce the X-ray dose, although the internal data of the second scanning range is collected at high X-ray dose, the external data of the second scanning range is collected at low X-ray dose. Some non-limiting examples are described below.

Figure 10A:
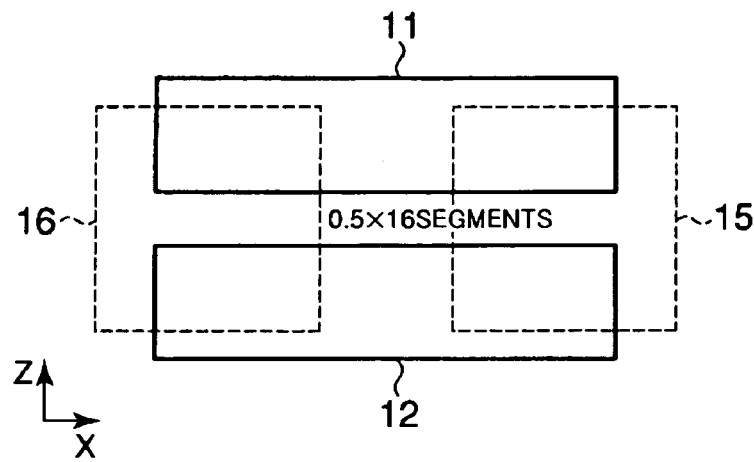
FIG. 10A through FIG. 10C are illustrations of openings of a collimator according to a method B.

A collimator shown in FIG. 10A has two collimator blades 11 and 12 that are used to limit the X-ray in the Z-direction and that include a lead member which is thick enough to block the X-ray. In addition, the collimator has other two collimator blades 15 and 16 that are used to limit the X-ray in the X-direction and that include a member whose attenuation coefficient is lower than that of lead, such as an Mo member or an alloyed metal member including lead. The collimator blades 15 and 16 block the X-ray in moderation. Thus, the high dose X-ray goes directly through the opening of the collimator 108 and is irradiated to the second scanning range, and the low dose X-ray attenuated by the semi-block collimator blades 15 and 16 is irradiated to the external area of the second scanning range. When the image is reconstructed, an X-ray dose correction is performed to the external data of the second scanning range, and the corrected external data and the internal data are used for the fan-beam reconstruction method with the HFI method.

Figure 10B:
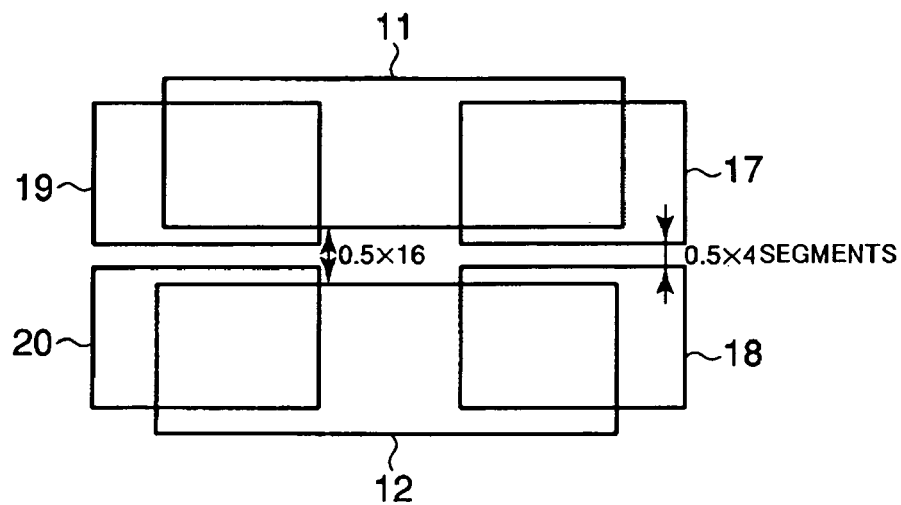

As another example, a collimator shown in FIG. 10B has two collimator blades 11 and 12 that are used to limit the X-ray in the Z-direction and has four collimator blades 17 through 20 that are movable in the X and Z directions for blocking the X-ray. The four collimator blades 17 through 20 are set on a position in the X-direction corresponding to the second scanning range, and are set at such a position in the Z-direction that a slit narrower than a central opening corresponding to the second scanning range is created. For instance, if the central opening is 8 mm (=0.5 mm×16 segments), the slit is created as 2 mm (=0.5 mm×4 segments). While the high dose X-ray directly passes through the opening of collimator 108 to the second scanning range, the thin X-ray limited by the slit is irradiated to the external area of the second scanning range. When the image is reconstructed, an X-ray dose correction is performed to the external data of the second scanning range, and the corrected external data and the internal data are used for the fan-beam reconstruction method with the HFI method.

Figure 10C:
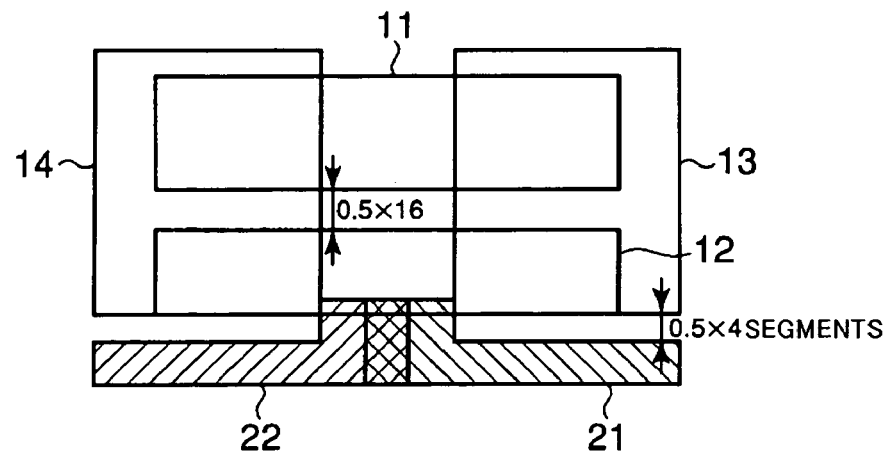

As another example, a collimator shown in FIG. 10C has a plurality of movable collimator blades 11 through 14 that create a central opening, and has a plurality of movable auxiliary blades 21 and 22, which create a slit corresponding to a part of detection element segments (four segments close to the outside) other than the central 16 detection element segments. That is, in addition to the four collimator blades 11–14 for limiting the X-ray in the Z-direction, the L-shaped two auxiliary blades 21 and 22 for blocking the X-ray block a central portion of the X-ray and open the peripheral part. The two auxiliary blades 21 and 22 are respectively movable in both X and Z directions, and shifted in the Y-direction so that it is possible to partially overlap on the central part. By adjusting the overlapped area on the central part, it is possible to arbitrarily change the central block area width. In the Z-direction, by adjusting the position of the four collimator blades 11 to 14, it is possible to open the slit at an arbitrary width out of the four collimator blades 11 to 14.

Thus, the two auxiliary blades 21 and 22 are set at such a position in the X-direction that the area has the same width as the opening created by the four collimator blades 11 to 14, and are set on such a position in the Z-direction that the slit narrower than the opening according to the second scanning range is created on the peripheral part. For example, if the opening created by the four collimator blades 11 to 14 according to the second scanning range is 8 mm (=0.5 mm×16 segments), the slit created by the auxiliary blades outside of the second scanning range is 2 mm (=0.5 mm×4 segments). Thus, the high dose X-ray goes directly through the opening created by the four collimator blades 11–14 to the second scanning range, and the two thin split X-rays limited by the auxiliary blades 21 and 22 are irradiated to the external area of the second scanning range. When the image is reconstructed, the external data and the internal data are used for the fan-beam reconstruction method with the HFI method. Since the external data of the second scanning range is shifted from the internal data in the Z-direction, the quality of the image may decrease near a border between the external and internal area. However, since the second scan is primarily used for an increasingly accurate diagnosis of the object internal organ and the external area of the second scanning range is not used for the diagnosis usually, there is substantially little negative influence.

In method B as well as method A, even if the center axis of the second scanning range is shifted from the rotation center axis RA of the rotation frame 102, as shown FIG. 11A to 11D, it is possible to continuously irradiate the high dose X-ray to the second scanning range by moving the collimator blade in the X-direction according to the rotation and by moving the irradiation range of the high dose X-ray to the second scanning range.

Figure 12:
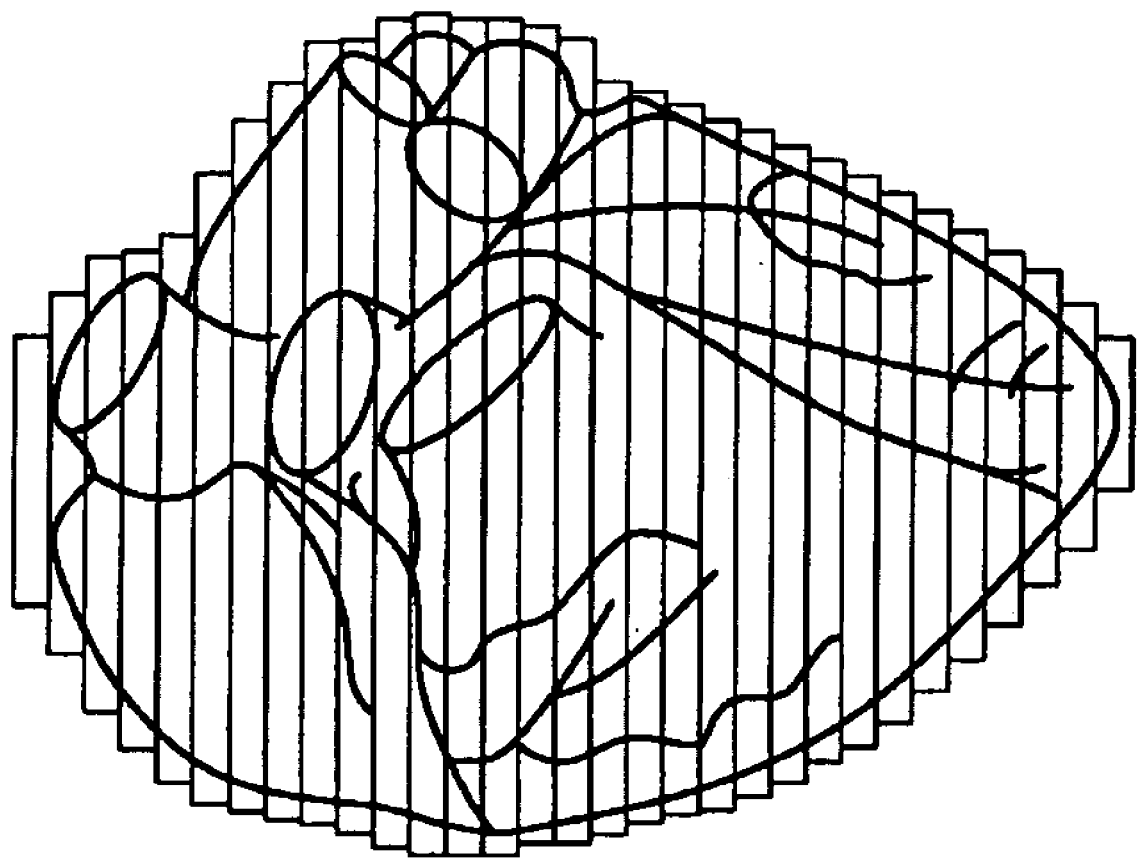
FIG. 12 is an illustration of another example of a display for setting the second scanning range on S7 of FIG. 2.
Figure 13:
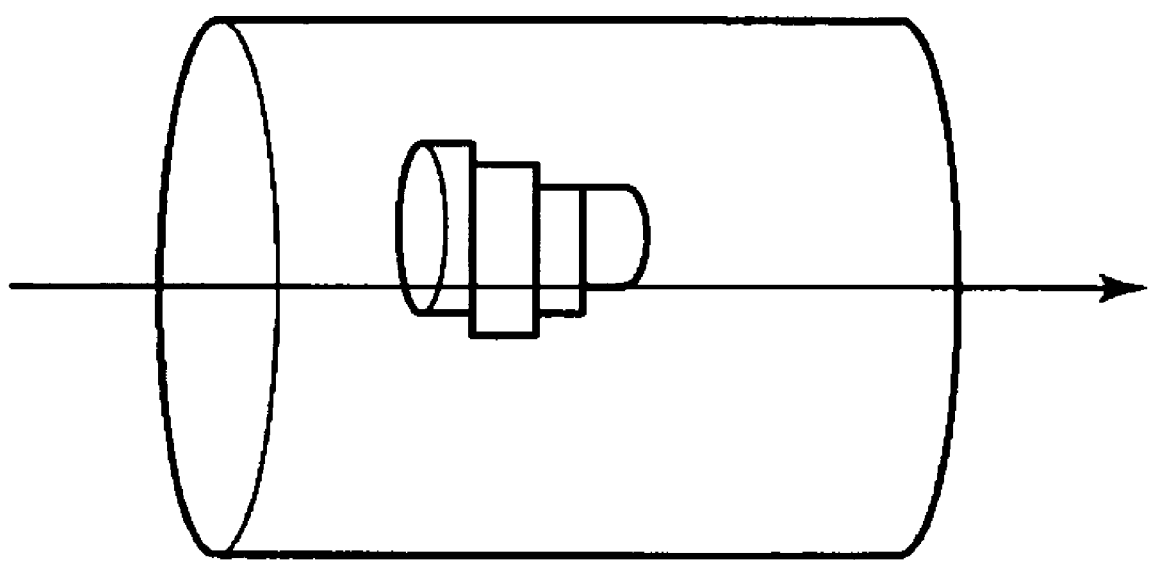
FIG. 13 is an illustration of first scanning range and second scanning range of FIG. 12.

It has been explained that the second scanning range is set as a cylinder form including the object internal organ, such as the heart. However, as shown in FIGS. 12 and 13, the diameter of the second scanning range may be changed according to the size of the object internal organ in the Z-direction. For example, the second scanning range may be set as a group of small cylinders, each of which has the length of the detection element segment pitch multiplied by the number of the segments, and the width of the opening of the collimator 108 may be changed according to the relative movement of the gantry 100 to the patient in the Z-direction by the helical scan in order to reduce the X-ray dose. In the non-limiting embodiment, the X-ray dose can be reduced in the multi slice X-ray CT apparatus.

Figure 14:
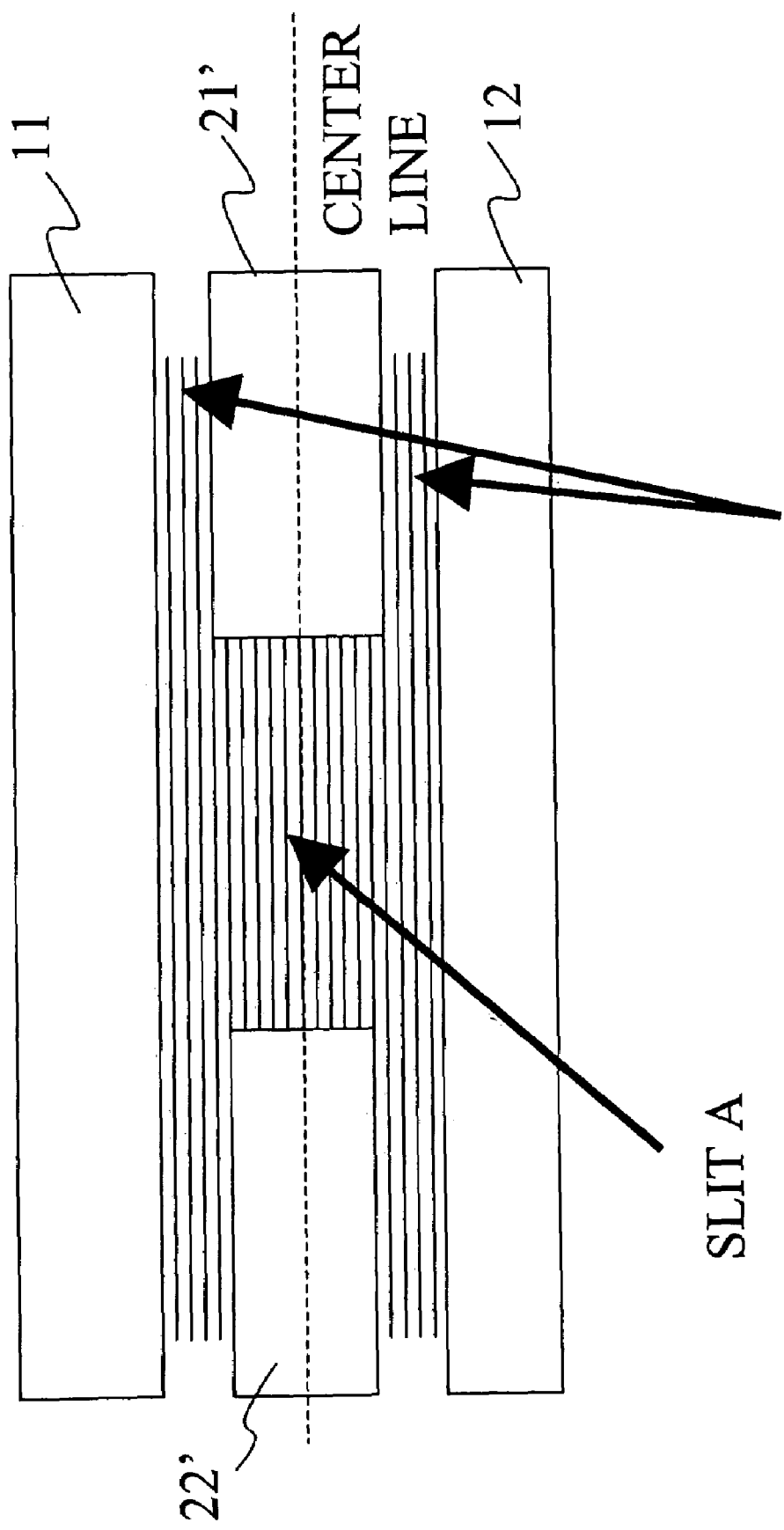
FIG. 14 is an illustration of an opening of another exemplary collimator.

Another non-limiting exemplary modification of the above mentioned embodiment is explained referring to FIG. 14. A collimator of the modification has a slit A in a center area for imaging the object internal organ, such as the heart, and has a plurality of movable auxiliary blades 21' and 22' for imaging a peripheral part of the object internal organ. An X-ray going through the slit A is irradiated to 16 central detection element segments, and an X-ray going through the slit B is irradiated to 4 detection element segments that are adjacent to the slit A in the slice direction and that have wider range in the channel direction than that of the slit A.

The image reconstruction unit 114 reconstructs the image data of the object internal organ, such as the heart of the patient, from data collected based on the X-ray which goes through the slit A, and reconstructs the image data of the peripheral part of the object internal organ, such as the heart of a patient, from data collected based on the X-ray which goes through the slit B. Image processing is performed by the image-processing unit 113 so that the image from the both image data is smoothly connected, and the image is displayed on the display 116.

The present invention may not be limited to the above embodiments, and various modifications may be made without departing from the spirit or scope of the general inventive concept. It is therefore to be understood that within the scope of the appended claims, the present invention may be practiced differently than as specifically described herein. Although the above embodiment and modification includes various steps or various elements, several steps or elements may be arbitrarily selected. For instance, some steps or elements described as the embodiment or modification may be omitted.

What is claimed is:

1. An X-ray CT apparatus, comprising:
   an X-ray irradiation source configured to irradiate X-rays to a volume of interest;
   an X-ray detector including a plurality of detection element segments configured to detect the X-rays penetrated through the volume of interest;
   a collimator configured to create an opening that is movable at least in a slice direction and a channel direction;
   an image processing part configured to generate volume data from the detected X-rays and to extract a portion of the volume data corresponding to the volume of interest;
   a controller configured to set the opening of the collimator to a first opening size to irradiate a first scanning range and configured to perform a first scan of the first scanning range, and to set the opening of the collimator in the channel direction to a second opening size to irradiate a second scanning range corresponding to the portion of the volume data and configured to perform a second scan of the second scanning range such that the second scanning range receives an amount of X-ray greater than an area external to the second scanning range; and
   a reconstruction part configured to reconstruct image data based on data collected by the second scan including data from the second scanning range and external data from an area within the first scanning range but external to the second scanning range.

2. The X-ray CT apparatus according to claim 1, wherein said controller is configured to set the opening of the collimator to a first opening size that is wider than the second opening size and to perform a first scan.

3. The X-ray CT apparatus according to claim 2, wherein the amount of the X-rays used on the first scan is lower than an amount of the X-rays used in the second scan.

4. The X-ray CT apparatus according to claim 2, wherein: the first scan includes a helical scan, the second scan includes a helical scan, and a helical pitch of the second scan is shorter than a helical pitch of the first scan.

5. The X-ray CT apparatus according to claim 2, wherein a number of the plurality of detection element segments used in the second scan is fewer than a number of the plurality of detection element segments used in the first scan.

6. The X-ray CT apparatus according to claim 2, wherein the reconstruction part compensates external data of the second scanning range with data collected by the first scan.

7. The X-ray CT apparatus according to claim 6, wherein the external data is collected during the second scan.

8. The X-ray CT apparatus according to claim 6, wherein the external data is collected based on an X-ray detected by detection element segments other than detection element segments used in the second scan.

9. An X-ray CT apparatus, comprising:
an X-ray irradiation source configured to irradiate X-rays to a volume of interest;
an X-ray detector including a plurality of detection element segments configured to detect the X-rays penetrated through the volume of interest;
a collimator configured to create an opening that is movable at least in a slice direction and a channel direction;
an image processing part configured to generate volume data from the detected X-rays and to extract a portion of the volume data corresponding to the volume of interest;
a controller configured to set the opening of the collimator to a first opening size to irradiate a first scanning range and configured to perform a first scan of the first scanning range, and to set the opening of the collimator in the channel direction to a second opening size to irradiate a second scanning range corresponding to the portion of the volume data and configured to perform a second scan of the second scanning range; and
a reconstruction part configured to reconstruct image data based on data collected by the second scan and external data in the first scanning range but outside the second scanning range.

* * * * *